United States Patent
Sawai

(10) Patent No.: US 10,220,043 B2
(45) Date of Patent: Mar. 5, 2019

(54) AQUEOUS COMPOSITION

(71) Applicant: KOWA COMPANY, LTD., Nagoya (JP)

(72) Inventor: Isamu Sawai, Fuji (JP)

(73) Assignee: KOWA COMPANY, LTD., Nagoya-shi (JP)

(*) Notice: Subject to any disclaimer, the term of this patent is extended or adjusted under 35 U.S.C. 154(b) by 12 days.

(21) Appl. No.: 15/534,069

(22) PCT Filed: Dec. 11, 2015

(86) PCT No.: PCT/JP2015/084802
§ 371 (c)(1),
(2) Date: Jun. 8, 2017

(87) PCT Pub. No.: WO2016/093344
PCT Pub. Date: Jun. 16, 2016

(65) Prior Publication Data
US 2017/0360799 A1 Dec. 21, 2017

(30) Foreign Application Priority Data

Dec. 12, 2014 (JP) ................................ 2014-251708

(51) Int. Cl.
| | | |
|---|---|---|
| *A61K 31/551* | (2006.01) | |
| *A61K 47/22* | (2006.01) | |
| *A61K 9/08* | (2006.01) | |
| *A61K 31/498* | (2006.01) | |
| *A61K 9/00* | (2006.01) | |
| *A61K 31/10* | (2006.01) | |
| *A61K 31/473* | (2006.01) | |
| *A61K 31/5513* | (2006.01) | |
| *A61P 27/06* | (2006.01) | |

(52) U.S. Cl.
CPC .......... *A61K 31/551* (2013.01); *A61K 9/0048* (2013.01); *A61K 9/08* (2013.01); *A61K 31/10* (2013.01); *A61K 31/473* (2013.01); *A61K 31/498* (2013.01); *A61K 31/5513* (2013.01); *A61K 47/22* (2013.01); *A61P 27/06* (2018.01)

(58) Field of Classification Search
CPC .................................................. A61K 31/551
See application file for complete search history.

(56) References Cited

U.S. PATENT DOCUMENTS

2006/0142270 A1* 6/2006 Sugimoto ............. A61K 31/55
514/218
2007/0088021 A1 4/2007 Hidaka et al.
2008/0234483 A1 9/2008 Maejima et al.
2009/0082338 A1* 3/2009 Mizuno ................. A61K 31/551
514/218
2017/0360782 A1 12/2017 Kaneko et al.

FOREIGN PATENT DOCUMENTS

| EP | 3 231 428 A1 | 10/2017 |
|---|---|---|
| JP | 2007-84474 A | 4/2007 |
| JP | 4212149 B2 | 1/2009 |
| JP | 2012-250953 A | 12/2012 |
| JP | 2013-35802 A | 2/2013 |
| WO | 2005/087237 A1 | 9/2005 |
| WO | 2006/068208 A1 | 6/2006 |
| WO | 2006/115244 A1 | 11/2006 |

OTHER PUBLICATIONS

International Search Report dated Mar. 1, 2016 in PCT/JP2015/084802 filed Dec. 11, 2015.
Saeki, Tadashiro et al., "Mouse Gan'atsu ni Taisuru Rock Sogaizai K115 to Brimonidine no Heiyo Koka," Japanese Society for Ocular Pharmacology Program Koen Shorokushu, vol. 27, 2007, 2 pages.
Extended European Search Report dated Jul. 6, 2018 in Patent Application No. 15867038.0, 7 pages.
Sato, S. et al. "Additive Intraocular Pressure Lowering Effects of the Rho Kinase Inhibitor, Ripasudil in Glaucoma Patients Not Able to Obtain Adequate Control After Other Maximal Tolerated Medical Therapy", Advances in Therapy, vol. 33, No. 9, XP036053879, Jul. 20, 2016, pp. 1628-1634.

* cited by examiner

*Primary Examiner* — Michael F Pepitone
(74) *Attorney, Agent, or Firm* — Oblon, McClelland, Maier & Neustadt, L.L.P.

(57) ABSTRACT

A technique is provided for suppressing the crystal precipitation of an aqueous composition containing a halogenated isoquinoline derivative during low-temperature preservation. An aqueous composition comprising a compound represented by Formula (1):

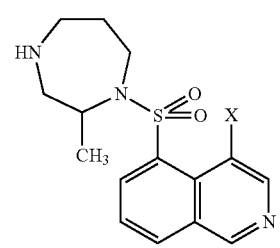

(1)

wherein x represents a halogen atom,
or a salt thereof, or a solvate of the compound or the salt thereof, and brimonidine or a salt thereof.

9 Claims, No Drawings

AQUEOUS COMPOSITION

CROSS REFERENCE TO RELATED APPLICATIONS

The present application is a 35 U.S.C. § 371 national stage patent application of International patent application PCT/JP2015/084802, filed on Dec. 11, 2015, and claims the benefit of the filing date of Japanese application No. 2014-251708, filed on Dec. 12, 2014.

TECHNICAL FIELD

The present invention relates to an aqueous composition and the like.

BACKGROUND ART

It is known that halogenated isoquinoline derivatives such as ripasudil (chemical name: 4-fluoro-5-{[(2S)-2-methyl-1,4-diazepan-1-yl]sulfonyl}isoquinoline) represented by the following structural formula:

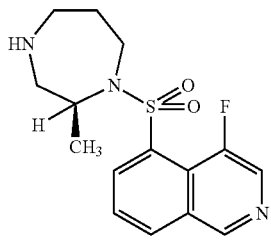 [SMILES: C[C@H]1CNCCCN1S(=O)(=O)c1cccc2cncc(F)c12]

and 4-bromo-5-{[(2S)-2-methyl-1,4-diazepan-1-yl]sulfonyl}isoquinoline represented by the following structural formula:

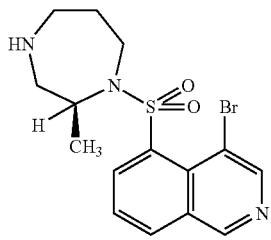 [SMILES: C[C@H]1CNCCCN1S(=O)(=O)c1cccc2cncc(Br)c12]

have pharmacological action such as Rho kinase inhibitory action (Patent Literatures 1 and 2, for example), and thus, are usable for the prevention or treatment of eye diseases. Specifically, for example, halogenated isoquinoline derivatives are reported to be suitable for prevention or treatment of ocular hypertension or glaucoma (Patent Literature 3, for example), for which reduction of intraocular pressure is effective.

Hence, it is extremely useful to establish a technique for producing stable preparations of these halogenated isoquinoline derivatives as ophthalmic agents, for example.

CITATION LIST

Patent Literature

[Patent Literature 1] JP-B-4212149
[Patent Literature 2] WO2006/115244
[Patent Literature 3] WO2006/068208

SUMMARY OF THE INVENTION

Technical Problem

An ophthalmic agent is generally a composition containing water (aqueous composition). To produce a preparation of a halogenated isoquinoline derivative, ripasudil, as an ophthalmic agent or the like, the present inventor initially prepared an aqueous composition containing ripasudil and the preservation stability was investigated, and as a result the aqueous composition was revealed to suffer from crystal precipitation due to low-temperature preservation.

Accordingly, it is an object of the present invention to provide a technique for suppressing the crystal precipitation of an aqueous composition containing a halogenated isoquinoline derivative during low-temperature preservation.

Solution to Problem

Thus, the present inventor conducted extensive research to solve the above-described problem, and found that further incorporation of brimonidine or a salt thereof in an aqueous composition containing a halogenated isoquinoline derivative such as ripasudil can suppress the crystal precipitation during low-temperature preservation, thus completing the present invention.

In summary, the present invention provides an aqueous composition comprising a compound represented by Formula (1):

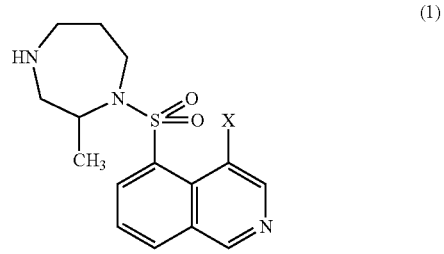

wherein X represents a halogen atom, or a salt thereof, or a solvate of the compound or the salt thereof, and brimonidine or a salt thereof.

Further, the present invention provides a method for suppressing crystal precipitation of an aqueous composition, the method comprising the step of incorporating brimonidine or a salt thereof in an aqueous composition containing a compound represented by Formula (1) or a salt thereof, or a solvate of the compound or the salt thereof.

Effects of Invention

In accordance with the present invention, the crystal precipitation of an aqueous composition containing a halogenated isoquinoline derivative such as ripasudil during low-temperature preservation can be suppressed.

DESCRIPTION OF EMBODIMENTS

The present specification discloses, although is in no way limited to, the following embodiments of invention, by way of example.

[1] An aqueous composition comprising a compound represented by Formula (1):

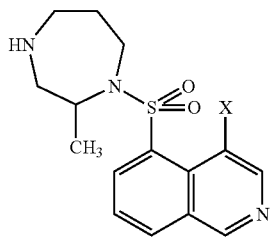

wherein X represents a halogen atom,
or a salt thereof, or a solvate of the compound or the salt thereof, and brimonidine or a salt thereof.

[2] The aqueous composition according to [1], wherein the compound represented by Formula (1) is ripasudil.

[3] The aqueous composition according to [1], wherein the compound represented by Formula (1) or a salt thereof or a solvate of the compound or the salt thereof is ripasudil hydrochloride.

[4] The aqueous composition according to any of [1] to [3], wherein the brimonidine or a salt thereof is brimonidine tartrate.

[5] The aqueous composition according to any of [1] to [4], being an ophthalmic agent.

[6] The aqueous composition according to any of [1] to [4], being an eye drop.

[7] The aqueous composition according to any of [1] to [6], being a prophylactic and/or therapeutic agent for ocular hypertension and/or glaucoma.

[8] The aqueous composition according to any of [1] to [7] which further contains one or more selected from the group consisting of a1 receptor blockers, α2 receptor agonists, β blockers, carbonic dehydrogenase inhibitors, prostaglandins, sympathomimetics, parasympathomimetics, calcium antagonists, and cholinesterase inhibitors.

[9] The aqueous composition according to any of [1] to [7], further containing one or more selected from the group consisting of tafluprost, travoprost, bimatoprost, latanoprost, nipradilol, timolol, bunazosin, dorzolamide, brinzolamide, isopropyl unoprostone, a salt of tafluprost, a salt of travoprost, a salt of bimatoprost, a salt of latanoprost, a salt of nipradilol, a salt of timolol, a salt of bunazosin, a salt of dorzolamide, a salt of brinzolamide, and a salt of isopropyl unoprostone.

[10] A method for suppressing crystal precipitation of an aqueous composition, the method comprising the step of incorporating brimonidine or a salt thereof in an aqueous composition containing the compound represented by Formula (1) or a salt thereof, or a solvate of the compound or the salt thereof.

[11] The method according to [10], wherein the compound represented by Formula (1) is ripasudil.

[12] The method according to [10], wherein the compound represented by Formula (1) or a salt thereof or a solvate of the compound or the salt thereof is ripasudil hydrochloride.

[13] The method according to any of [10] to [12], wherein the brimonidine or a salt thereof is brimonidine tartrate.

[14] The method according to any of [10] to [12], wherein the aqueous composition is an ophthalmic agent.

[15] The method according to any of [10] to [12], wherein the aqueous composition is an eye drop.

[16] The method according to any of [10] to [15], wherein the aqueous composition is a prophylactic and/or therapeutic agent for ocular hypertension and/or glaucoma.

[17] The method according to any of [10] to [16], wherein the aqueous composition further contains one or more selected from the group consisting of α1 receptor blockers, α2 receptor agonists, β blockers, carbonic dehydrogenase inhibitors, prostaglandins, sympathomimetics, parasympathomimetics, calcium antagonists, and cholinesterase inhibitors.

[18] The method according to any of [10] to [17], wherein the aqueous composition further contains one or more selected from the group consisting of tafluprost, travoprost, bimatoprost, latanoprost, nipradilol, timolol, bunazosin, dorzolamide, brinzolamide, isopropyl unoprostone, a salt of tafluprost, a salt of travoprost, a salt of bimatoprost, a salt of latanoprost, a salt of nipradilol, a salt of timolol, a salt of bunazosin, a salt of dorzolamide, a salt of brinzolamide, and a salt of isopropyl unoprostone.

Examples of the halogen atom in Formula (1) include a fluorine atom, a chlorine atom, and a bromine atom. In Formula (1), a fluorine atom or a bromine atom is preferred as the halogen atom, and a fluorine atom is particularly preferred.

Further, in Formula (1), the carbon atom forming the homopiperazine ring substituted with the methyl group is an asymmetric carbon atom. As a result, stereoisomerism occurs. The compound represented by Formula (1) includes all the stereoisomers, and may be a single stereoisomer or a mixture of various stereoisomers at any given ratio. Preferred as the compound represented by Formula (1) is a compound having the S configuration as the absolute configuration.

The salt of the compound represented by Formula (1) is not particularly limited as long as it is a pharmacologically acceptable salt, and specific examples of the salt include inorganic acid salts such as hydrochloride, sulfate, nitrate, hydrofluoride, and hydrobromate; and organic acid salts such as acetate, tartrate, lactate, citrate, fumarate, maleate, succinate, methanesulfonate, ethanesulfonate, benzenesulfonate, toluenesulfonate, naphthalenesulfonate, and camphorsulfonate, with hydrochloride being preferred.

The compound represented by Formula (1) or a salt thereof may also be in the form of a hydrate or a solvate such as an alcohol solvate, and is preferably in the form of a hydrate.

Specific examples of the compound represented by Formula (1) or a salt thereof or a solvate of the compound or the salt thereof include: ripasudil (chemical name: 4-fluoro-5-{[(2S)-2-methyl-1,4-diazepan-1-yf]sulfonyl}isoquinoline) or a salt thereof or a solvate of ripasudil or the salt thereof; and 4-bromo-5-{[(2S)-2-methyl-1,4-diazepan-1-yl] sulfonyl}isoquinoline or a salt thereof or a solvate of 4-bromo-5-{[(2S)-2-methyl-1,4-diazepan-1-yl] sulfonyl}isoquinoline or the salt thereof.

The compound represented by Formula (1) or a salt thereof or a solvate thereof is preferably ripasudil or a salt thereof or a solvate of ripasudil or the salt thereof, or 4-bromo-5-{[(2S)-2-methyl-1,4-diazepan-1-yl] sulfonyl}isoquinoline or a salt thereof or a solvate of 4-bromo-5-{[(2S)-2-methyl-1,4-diazepan-1-yl] sulfonyl}isoquinoline or the salt thereof, more preferably ripasudil or a salt thereof or a solvate of ripasudil or the salt thereof, still more preferably ripasudil or a hydrochloride thereof or a hydrate of ripasudil or the hydrochloride thereof, and particularly preferably a ripasudil hydrochloride hydrate (ripasudil monohydrochloride dihydrate) represented by the following structural formula:

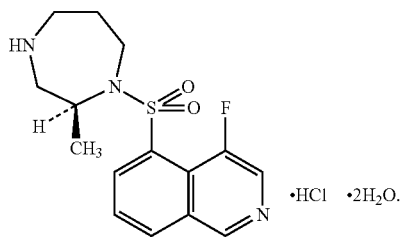

The compound represented by Formula (1) or a salt thereof or a solvate of the compound or the salt thereof is known and can be produced using a known method. Specifically, ripasudil or a salt thereof or a solvate of ripasudil or the salt thereof can be produced using the method described in WO1999/020620 or WO2006/057397, for example. 4-Bromo-5-{[(2S)-2-methyl-1,4-diazepan-1-yl]sulfonyl}isoquinoline or a salt thereof or a solvate of 4-bromo-5-{[(2S)-2-methyl-1,4-diazepan-1-yl]sulfonyl}isoquinoline or the salt thereof can be produced using the method described in WO2006/115244, for example.

The content of the compound represented by Formula (1) or a salt thereof or a solvate of the compound or the salt thereof in the aqueous composition is not particularly limited, and may be determined as appropriate, in consideration of the target disease, or the sex, age, or symptoms of the patient, for example. From the viewpoint of achieving excellent pharmacological action, however, the content of the compound represented by Formula (1) or a salt thereof or a solvate of the compound or the salt thereof is preferably 0.01 to 10 w/v %, more preferably 0.02 to 8 w/v %, and particularly preferably 0.04 to 6 w/v %, calculated as the free form of the compound represented by Formula (1), based on the total volume of the aqueous composition. In particular, when ripasudil is used as the compound represented by Formula (1), from the viewpoint of achieving excellent pharmacological action, the content of ripasudil or a salt thereof or a solvate of ripasudil or the salt thereof is preferably 0.05 to 5 w/v %, more preferably 0.1 to 3 w/v %, and particularly preferably 0.15 to 2 w/v %, calculated as the free form, based on the total volume of the aqueous composition.

As used herein, "brimonidine or a salt thereof" includes not only brimonidine but also pharmaceutically acceptable salts of brimonidine. Each of them is a known compound, and can be produced using a known method, for example, described in U.S. Pat. No. 3,890,319, and a commercially available product can be used.

Specific examples of pharmaceutically acceptable salts include inorganic acid salts such as hydrochloride, sulfate, nitrate, hydrofluoride, and hydrobromate; and organic acid salts such as acetate, tartrate, lactate, citrate, fumarate, maleate, succinate, methanesulfonate, ethanesulfonate, benzenesulfonate, toluenesulfonate, naphthalenesulfonate, and camphorsulfonate, with tartrate being preferred. In the present invention, brimonidine or brimonidine tartrate (brimonidine monotartrate) (chemical name: 5-bromo-N-(4,5-dihydro-1H-imidazol-2-yl)quinoxaline-6-amine mono-(2R, 3R)-tartrate) is preferred as brimonidine or a salt thereof.

While the content of brimonidine or a salt thereof in the aqueous composition is not particularly limited, from the viewpoint of crystal precipitation-suppressing action and in addition the intraocular pressure-reducing action of brimonidine or a salt thereof, the content of brimonidine or a salt thereof is preferably 0.01 to 1 w/v %, more preferably 0.02 to 0.5 w/v %, and particularly preferably 0.03 to 0.1 w/v %, calculated as the free form of brimonidine, based on the total volume of the aqueous composition.

While the content ratio by mass of brimonidine or a salt thereof to the compound represented by Formula (1) or a salt thereof or a solvate of brimonidine or the salt thereof in the aqueous composition is not particularly limited, for example, from the viewpoint of crystal precipitation-suppressing action, the content ratio by mass of brimonidine or a salt thereof is preferably 0.01 to 1.5 parts by mass, more preferably 0.04 to 0.8 parts by mass, and particularly preferably 0.08 to 0.3 parts by mass, calculated as the free form of brimonidine, with respect to 1 part by mass of the compound represented by Formula (1) calculated as the free form. In particular, when the compound represented by Formula (1) or a salt thereof or a solvate of the compound or the salt thereof is ripasudil or a salt thereof or a solvate of ripasudil or the salt thereof, for example, from the viewpoint of crystal precipitation-suppressing action, the content ratio by mass of brimonidine or a salt thereof is preferably 0.02 to 1 parts by mass, more preferably 0.06 to 0.5 parts by mass, and particularly preferably 0.1 to 0.2 parts by mass, calculated as the free form of brimonidine, with respect to 1 part by mass of ripasudil calculated as the free form.

As specifically disclosed in Test Example 1, it was found that, although the aqueous composition containing the compound represented by Formula (1) typified by ripasudil or a salt thereof or a solvate of the compound or the salt thereof can suffer from crystal precipitation during low-temperature preservation, further incorporation of brimonidine or a salt thereof in such an aqueous composition suppresses crystal precipitation during low-temperature preservation in comparison with the case where the aqueous composition does not contain brimonidine or a salt thereof. Accordingly, the aqueous composition containing the compound represented by Formula (1) or a salt thereof or a solvate of the compound or the salt thereof and brimonidine or a salt thereof is suppressed from crystal precipitation during low-temperature preservation, and thus has an advantage of excellent preservation stability.

While the intraocular pressure-lowering action of the compound represented by Formula (1) typified by ripasudil, or a salt thereof or a solvate of the compound or the salt thereof and that of brimonidine or a salt thereof are combined to produce further excellent intraocular pressure-lowering action, which is extremely useful for ocular hypertension and glaucoma, these components can be incorporated in a single preparation to produce a combined drug, without combined use of them, which is fairly advantageous from the viewpoint of preventing poor compliance in therapy.

As used herein, the "aqueous composition" means a composition containing at least water, which may be in the form of a liquid (solution or suspension) or a semi-solid (ointment), for example, and preferably in the form of a liquid. As the water in the composition, purified water, water for injection, or sterile purified water, for example, can be used.

While the content of water in the aqueous composition is not particularly limited, it is preferably 5 mass % or more, more preferably 20 mass % or more, still more preferably 50 mass % or more, even more preferably 90 mass % or more, and particularly preferably 90 to 99.8 mass %.

The aqueous composition can be prepared into various dosage forms in accordance with known methods described in the General Rules for Preparations in the Japanese Pharmacopoeia 16$^{th}$ Edition, for example. Examples of dosage forms include injections, inhalation solutions, eye drops, eye ointments, ear drops, nasal drops, enemas, liquids for external use, sprays, ointments, gels, oral liquids, and syrups. From the viewpoint of advantageously utilizing the pharmacological action of the compound represented by Formula (1), the dosage form is an ophthalmic agent, which specifically is preferably an eye drop or an eye ointment, and is particularly preferably an eye drop.

The aqueous composition may contain, in addition to the components described above, additives used in drugs, quasi drugs, and the like, in accordance with the dosage form. Examples of such additives include inorganic salts, isotonic agents, chelating agents, stabilizers, pH regulators, antiseptics, antioxidants, thickeners, surfactants, solubilizers, suspending agents, cooling agents, dispersants, preservatives, oily bases, emulsion bases, and water-soluble bases.

Specific examples of these additives include ascorbic acid, potassium aspartate, sodium bisulfite, alginic acid, sodium benzoate, benzyl benzoate, epsilon-aminocaproic acid, fennel oil, ethanol, ethylene-vinyl acetate copolymer, sodium edetate, tetrasodium edetate, potassium chloride, calcium chloride hydrate, sodium chloride, magnesium chloride, hydrochloric acid, alkyl diaminoethylglycine hydrochloride solution, carboxyvinyl polymer, dried sodium sulfite, dried sodium carbonate, d-camphor, dl-camphor, xylitol, citric acid hydrate, sodium citrate hydrate, glycerin, gluconic acid, L-glutamic acid, monosodium L-glutamate, creatinine, chlorhexidine gluconate solution, chlorobutanol, sodium dihydrogenphosphate dihydrate, geraniol, sodium chondroitin sulfate, acetic acid, potassium acetate, sodium acetate hydrate, titanium oxide, gellan gum, dibutylhydroxytoluene, potassium bromide, benzododecinium bromide, tartaric acid, sodium hydroxide, polyoxyl 45 stearate, purified lanolin, D-sorbitol, sorbitol solution, taurine, sodium bicarbonate, sodium carbonate hydrate, sodium thiosulfate hydrate, thimerosal, tyloxapol, sodium dehydroacetate, trometamol, concentrated glycerin, mixed tocopherol concentrate, white petrolatum, mentha water, mentha oil, benzalkonium chloride concentrated solution 50, ethyl parahydroxybenzoate, butyl parahydroxybenzoate, propyl parahydroxybenzoate, methyl parahydroxybenzoate, sodium hyaluronate, human serum albumin, hydroxyethyl cellulose, hydroxypropyl cellulose, hypromellose, glacial acetic acid, sodium pyrosulfite, phenylethyl alcohol, glucose, propylene glycol, bergamot oil, benzalkonium chloride, benzalkonium chloride solution, benzyl alcohol, benzethonium chloride, benzethonium chloride solution, borax, boric acid, povidone, polyoxyethylene (200) polyoxypropylene glycol (70), sodium polystyrene sulfonate, polysorbate 80, polyoxyethylene hydrogenated castor oil 60, partially hydrolyzed polyvinyl alcohol, d-borneol, macrogol 4000, macrogol 6000, D-mannitol, anhydrous citric acid, anhydrous sodium monohydrogen phosphate, anhydrous sodium dihydrogen phosphate, methanesulfonic acid, methylcellulose, l-menthol, monoethanolamine, aluminum monostearate, polyethylene glycol monostearate, *eucalyptus* oil, potassium iodide, sulfuric acid, oxyquinoline sulfate, liquid paraffin, borneo camphor, phosphoric acid, dibasic sodium phosphate hydrate, potassium dihydrogenphosphate, sodium dihydrogen phosphate, sodium dihydrogen phosphate monohydrate, malic acid, and petrolatum.

Examples of preferred additives include potassium chloride, calcium chloride hydrate, sodium chloride, magnesium chloride, glycerin, acetic acid, potassium acetate, sodium acetate hydrate, tartaric acid, sodium hydroxide, sodium bicarbonate, sodium carbonate hydrate, concentrated glycerin, hydroxyethyl cellulose, hydroxypropyl cellulose, hypromellose, borax, boric acid, povidone, polysorbate 80, polyoxyethylene hydrogenated castor oil, polyethylene glycol monostearate, partially hydrolyzed polyvinyl alcohol, macrogol 4000, macrogol 6000, D-mannitol, anhydrous citric acid, anhydrous sodium monohydrogen phosphate, anhydrous sodium dihydrogen phosphate, methylcellulose, monoethanolamine, phosphoric acid, dibasic sodium phosphate hydrate, potassium dihydrogenphosphate, sodium dihydrogen phosphate, sodium dihydrogenphosphate monohydrate, sodium hyaluronate, glucose, and l-menthol.

The aqueous composition may further contain, in addition to the components described above, other medicinal components in accordance with the target disease and the like. Examples of such medicinal components include α1 receptor blockers including bunazosin or a salt thereof or a solvate of bunazosin or the salt thereof, such as bunazosin hydrochloride; α2 receptor agonists including apraclonidine or a salt thereof or a solvate of apraclonidine or the salt thereof; β blockers including carteolol or a salt thereof or a solvate of carteolol or the salt thereof, such as carteolol hydrochloride, nipradilol or a salt thereof or a solvate of nipradilol or the salt thereof, timolol or a salt thereof or a solvate of timolol or the salt thereof, such as timolol maleate, betaxolol or a salt thereof or a solvate thereof, such as betaxolol hydrochloride, levobunolol or a salt thereof or a solvate of levobunolol or the salt thereof, such as levobunolol hydrochloride, befunolol or a salt thereof or a solvate of befunolol or the salt thereof, and metipranolol or a salt thereof or a solvate of metipranolol or the salt thereof; carbonic anhydrase inhibitors including dorzolamide or a salt thereof or a solvate of dorzolamide or the salt thereof, such as dorzolamide hydrochloride, brinzolamide or a salt thereof or a solvate of brinzolamide or the salt thereof, acetazolamide or a salt thereof or a solvate of acetazolamide or the salt thereof, dichlorphenamide or a salt thereof or a solvate of dichlorphenamide or the salt thereof, and methazolamide or a salt thereof or a solvate of methazolamide or the salt thereof; prostaglandins including isopropyl unoprostone or a salt thereof or a solvate of isopropyl unoprostone or the salt thereof, tafluprost or a salt thereof or a solvate of tafluprost or the salt thereof, travoprost or a salt thereof or a solvate of travoprost or the salt thereof, bimatoprost or a salt thereof or a solvate of bimatoprost or the salt thereof, and latanoprost or a salt thereof or a solvate of latanoprost or the salt thereof; sympathomimetics including dipivefrine or a salt thereof or a solvate of dipivefrine or the salt thereof, such as dipivefrine hydrochloride, and epinephrine or a salt thereof or a solvate of epinephrine or the salt thereof, such as epinephrine, epinephrine borate, or epinephrine hydrochloride; parasympathomimetics including distigmine bromide or a salt thereof or a solvate of distigmine bromide or the salt thereof, pilocarpine or a salt thereof or a solvate of pilocarpine or the salt thereof, such as pilocarpine, pilocarpine hydrochloride, or pilocarpine nitrate, and carbachol or a salt thereof or a solvate of carbachol or the salt thereof; calcium antagonists including lomerizine or a salt thereof or a solvate of lomerizine or the salt thereof, such as lomerizine hydrochloride; and cholinesterase inhibitors including demecarium or a salt thereof or a solvate of demecarium or the salt thereof, echothiophate or a salt thereof or a solvate of echothiophate or the salt thereof, and physostigmine or a salt thereof or a solvate of physostigmine or the salt thereof. One or more of these medicinal components can be incorporated.

Preferred as the other medicinal component is one or more selected from the group consisting of tafluprost, travoprost, bimatoprost, latanoprost, nipradilol, timolol, bunazosin, dorzolamide, brinzolamide, and isopropyl unoprostone, a salt of tafluprost, a salt of travoprost, a salt of bimatoprost, a salt of latanoprost, a salt of nipradilol, a salt of timolol, a salt of bunazosin, a salt of dorzolamide, a salt of brinzolamide, a salt of isopropyl unoprostone, a solvate of tafluprost or the salt thereof, a solvate of travoprost or the salt thereof, a solvate of bimatoprost or the salt thereof, a solvate of latanoprost or the salt thereof, a solvate of nipradilol or the salt thereof, a solvate of timolol or the salt thereof, a solvate of bunazosin or the salt thereof, a solvate of dorzolamide or the salt thereof, a solvate of brinzolamide or the salt thereof, and a solvate of isopropyl unoprostone or the salt thereof, and more preferred is one or more selected from the group consisting of nipradilol, timolol, bunazosin, dorzolamide, brinzolamide, isopropyl unoprostone, a salt of nipradilol, a salt of timolol, a salt of bunazosin, a salt of dorzolamide, a salt of brinzolamide, a salt of isopropyl unoprostone, a solvate of nipradilol or the salt thereof, a solvate of timolol or the salt thereof, a solvate of bunazosin or the salt thereof, a solvate of dorzolamide or the salt thereof, a solvate of brinzolamide or the salt thereof, and a solvate of isopropyl unoprostone or the salt thereof.

The pH of the aqueous composition is not particularly limited, but is preferably 4 to 9, more preferably 4.5 to 8, and particularly preferably 5 to 7. The osmotic pressure ratio of the aqueous composition relative to physiological saline is not particularly limited, but is preferably 0.6 to 3, and particularly preferably 0.6 to 2.

The aqueous composition is preferably stored in a container, from the viewpoint of preservation stability and portability, and the like. The form of the container is not particularly limited as long as it can store an aqueous composition, and may be selected or set as appropriate, depending on the dosage form, for example. Specific examples of such forms of the container include containers for injections, containers for inhalations, containers for sprays, bottle-shaped containers, tubular containers, containers for eye drops, containers for nasal drops, containers for ear drops, and bag containers. The container may be further packaged in a box, a bag, or the like.

The material of the container is not particularly limited, and may be selected as appropriate depending on the form of the container. Specific examples of materials include glass, plastics, cellulose, pulp, rubber, and metals, and preferably a plastic from the viewpoint of processability, squeezability, and durability. The resin for a container made of a plastic is preferably a thermoplastic resin. Examples of such resins include polyolefin-based resins such as low-density polyethylene (including linear low-density polyethylene), high-density polyethylene, medium-density polyethylene, polypropylene, and cyclic polyolefins; polyester-based resins such as polyethylene terephthalate, polybutylene terephthalate, polyethylene naphthalate, polybutylene naphthalate, and poly(1,4-cyclohexylene dimethylene terenaphthalate); polyphenylene ether-based resins; polycarbonate-based resins; polysulfone-based resins; polyamide-based resins; polyvinyl chloride resins; and styrene-based resins. A mixture of these resins (polymer alloy) may also be used.

The disease targeted by the aqueous composition is not particularly limited, and may be selected as appropriate depending on the pharmacological action or the like of the compound represented by Formula (1).

Specifically, the aqueous composition can be used, for example, as a prophylactic or therapeutic agent for ocular hypertension or glaucoma, based on the Rho kinase inhibitory action or intraocular pressure-lowering action of the compound represented by Formula (1). More specifically, examples of types of glaucoma include primary open-angle glaucoma, normal-tension glaucoma, hypersecretion glaucoma, acute closed-angle glaucoma, chronic closed-angle glaucoma, plateau iris syndrome, combined mechanism glaucoma, steroid-induced glaucoma, capsular glaucoma, pigmentary glaucoma, amyloid-associated glaucoma, neovascular glaucoma, and malignant glaucoma.

When the aqueous composition according to the present invention is used as an agent for an eye disease, it may be administered once or twice per day, and is preferably administered twice per day.

EXAMPLES

The present invention will be described next in more detail with reference to examples; however, the invention is in no way limited to these examples.

In the following test examples, ripasudil monohydrochloride dihydrate can be produced in accordance with the method described in WO2006/057397, for example. Brimonidine tartrate can be produced, for example, using a method described in U.S. Pat. No. 3,890,319.

[Test Example 1] Preservation Test

Aqueous compositions of the formulations shown in Table 1 were prepared in accordance with a conventional method, and preserved at −5° C., during which the presence or absence of crystal precipitation was visually evaluated periodically to determine for which aqueous composition earlier crystal precipitation would be observed. The aqueous composition for which earlier crystal precipitation was not observed was rated as "b", and the aqueous composition for which earlier crystal precipitation was observed was rated as "d". The results are shown in Table 1.

TABLE 1

| | Quantity (per 100 mL) | |
| --- | --- | --- |
| | Example 1 | Comparative Example 1 |
| Ripasudil Monohydrochloride Dihydrate | 0.9792 g (0.8 g as the free form) | 0.9792 g (0.8 g as the free form) |
| Brimonidine Tartrate | 0.2 g | — |
| Anhydrous Sodium Dihydrogen Phosphate | 0.4 g | 0.4 g |
| Benzalkonium Chloride Concentrated Solution 50 | 0.002 mL | 0.002 mL |
| Sodium Hydroxide | q.s. (pH 6.0) | q.s. (pH 6.0) |
| Purified Water | Total Amount 100 mL | Total Amount 100 mL |
| Crystal Precipitation | b | d |

As shown in the results set forth in Table 1, it was revealed that when brimonidine tartrate was further incorporated in the aqueous composition containing ripasudil, crystal precipitation during low-temperature preservation was suppressed in comparison with the case where the aqueous composition does not contain brimonidine tartrate.

The foregoing test results revealed that when brimonidine or a salt thereof is further incorporated in the aqueous composition containing the compound represented by Formula (1) typified by ripasudil or a salt thereof or a solvate of the compound or the salt thereof, precipitation of crystals is relatively difficult to occur even after preservation at low temperature, and excellent preservation stability can be achieved.

Production Examples 1 to 27

Aqueous compositions containing the components in the quantities (amounts (g) per 100 mL of the aqueous composition) shown in Tables 2 to 4 can be produced in accordance with a conventional method.

TABLE 2

|  | Production Example 1 | Production Example 2 | Production Example 3 | Production Example 4 | Production Example 5 | Production Example 6 | Production Example 7 | Production Example 8 | Production Example 9 |
|---|---|---|---|---|---|---|---|---|---|
| Ripasudil Monohydrochloride Dihydrate (as the amount of the free form) | 0.2 | 0.2 | 0.2 | 0.4 | 0.4 | 0.4 | 0.8 | 0.8 | 0.8 |
| Brimonidine Tartrate | 0.1 | 0.1 | 0.1 | 0.1 | 0.1 | 0.1 | 0.1 | 0.1 | 0.1 |
| Sodium Chloride | 0.65 | — | — | — | 0.3 | 0.3 | 0.3 | 0.3 | — |
| Glycerin | — | 2 | — | — | 1 | — | — | 0.5 | 1 |
| Propylene Glycol | — | — | 2 | — | — | 1 | — | 0.5 | 1 |
| Potassium Chloride | — | — | — | 0.6 | — | — | 0.3 | — | — |
| Sodium Dihydrogenphosphate Monohydrate | 0.4 | 0.4 | 0.4 | — | — | 0.4 | 0.4 | 0.4 | 0.4 |
| Dibasic Sodium Phosphate Hydrate | — | — | — | — | — | — | — | q.s. | q.s. |
| Anhydrous Sodium Monohydrogen Phosphate | — | — | — | — | — | q.s. | q.s. | — | — |
| Potassium Dihydrogenphosphate | — | — | — | 0.4 | 0.4 | — | — | — | — |
| Sodium Hydroxide | q.s. | q.s. | q.s. | q.s. | q.s. | — | — | — | — |
| Hydrochloric Acid | — | — | — | — | — | — | q.s. | q.s. | q.s. |
| Citric Acid Hydrate | 0.1 | — | — | — | — | 0.1 | — | — | — |
| Sodium Acetate Hydrate | — | 0.1 | — | — | — | 0.1 | — | — | — |
| Sodium Edetate | — | — | — | 0.1 | — | — | 0.1 | — | — |
| Benzalkonium Chloride | 0.001 | 0.005 | — | 0.001 | 0.005 | 0.01 | 0.001 | 0.005 | — |
| Benzethonium Chloride | — | — | — | — | — | — | — | — | 0.01 |
| Methyl Parahydroxybenzoate | — | — | 0.01 | — | — | — | 0.01 | — | — |
| Propyl Parahydroxybenzoate | — | — | 0.01 | — | — | — | 0.01 | — | — |
| Chlorobutanol | — | — | — | 0.2 | — | — | — | 0.2 | — |
| Polysorbate 80 | 0.3 | — | — | 0.3 | 0.3 | — | — | 0.3 | 0.3 |
| Polyoxyethylene Castor Oil 60 | — | 0.3 | — | 0.3 | — | 0.3 | — | 0.3 | 0.3 |
| Polyethylene Glycol Monostearate | — | — | 1.5 | 1.5 | — | — | 1.5 | — | 1.5 |
| Purified Water | Total Amount 100 mL | Total Amount 100 mL | Total Amount 100 mL | Total Amount 100 mL | Total Amount 100 mL | Total Amount 100 mL | Total Amount 100 mL | Total Amount 100 mL | Total Amount 100 mL |
| pH | 5 | 5 | 6 | 6 | 6.5 | 6.5 | 4.5 | 4.5 | 4 |

TABLE 3

|  | Production Example 10 | Production Example 11 | Production Example 12 | Production Example 13 | Production Example 14 | Production Example 15 | Production Example 16 | Production Example 17 | Production Example 18 |
|---|---|---|---|---|---|---|---|---|---|
| Ripasudil Monohydrochloride Dihydrate (as the amount of the free form) | 0.2 | 0.2 | 0.2 | 0.4 | 0.4 | 0.4 | 0.8 | 0.8 | 0.8 |
| Brimonidine Tartrate | 0.1 | 0.1 | 0.1 | 0.1 | 0.1 | 0.1 | 0.1 | 0.1 | 0.1 |
| Sodium Chloride | 0.65 | — | — | — | 0.3 | 0.3 | 0.3 | 0.3 | — |
| Glycerin | — | 2 | — | — | 1 | — | — | 0.5 | 1 |
| Propylene Glycol | — | — | 2 | — | — | 1 | — | 0.5 | 1 |
| Potassium Chloride | — | — | — | 0.6 | — | — | 0.3 | — | — |
| Boric Acid | 1.0 | 1.0 | 1.0 | 1.0 | 1.0 | 1.0 | 1.0 | 1.0 | 1.0 |
| Borax | — | — | — | — | q.s. | q.s. | — | — | — |
| Sodium Hydroxide | q.s. | q.s. | q.s. | q.s. | — | — | — | — | — |
| Hydrochloric Acid | — | — | — | — | — | — | q.s. | q.s. | q.s. |
| Citric Acid Hydrate | 0.1 | — | — | — | — | 0.1 | — | — | — |
| Sodium Acetate Hydrate | — | 0.1 | — | — | — | 0.1 | — | — | — |
| Sodium Edetate | — | — | — | 0.1 | — | — | 0.1 | — | — |
| Benzalkonium Chloride | 0.001 | 0.005 | — | 0.001 | 0.005 | 0.01 | 0.001 | 0.005 | — |
| Benzethonium Chloride | — | — | — | — | — | — | — | — | 0.01 |
| Methyl Parahydroxybenzoate | — | — | 0.01 | — | — | — | 0.01 | — | — |
| Propyl Parahydroxybenzoate | — | — | 0.01 | — | — | — | 0.01 | — | — |
| Chlorobutanol | — | — | — | 0.2 | — | — | — | 0.2 | — |
| Polysorbate 80 | 0.3 | — | — | 0.3 | 0.3 | — | — | 0.3 | 0.3 |

TABLE 3-continued

|  | Production Example 10 | Production Example 11 | Production Example 12 | Production Example 13 | Production Example 14 | Production Example 15 | Production Example 16 | Production Example 17 | Production Example 18 |
|---|---|---|---|---|---|---|---|---|---|
| Polyoxyethylene Castor Oil 60 | — | 0.3 | — | 0.3 | — | 0.3 | — | 0.3 | 0.3 |
| Polyethylene Glycol Monostearate | — | — | 1.5 | 1.5 | — | — | 1.5 | — | 1.5 |
| Purified Water | Total Amount 100 mL | Total Amount 100 mL | Total Amount 100 mL | Total Amount 100 mL | Total Amount 100 mL | Total Amount 100 mL | Total Amount 100 mL | Total Amount 100 mL | Total Amount 100 mL |
| pH | 5 | 5 | 6 | 6 | 6.5 | 6.5 | 4.5 | 4.5 | 4 |

TABLE 4

|  | Production Example 19 | Production Example 20 | Production Example 21 | Production Example 22 | Production Example 23 | Production Example 24 | Production Example 25 | Production Example 26 | Production Example 27 |
|---|---|---|---|---|---|---|---|---|---|
| Ripasudil Monohydrochloride Dihydrate (as the amount of the free form) | 0.2 | 0.2 | 0.2 | 0.4 | 0.4 | 0.4 | 0.8 | 0.8 | 0.8 |
| Brimonidine Tartrate | 0.1 | 0.1 | 0.1 | 0.1 | 0.1 | 0.1 | 0.1 | 0.1 | 0.1 |
| Sodium Chloride | 0.65 | — | — | — | 0.3 | 0.3 | 0.3 | 0.3 | — |
| Glycerin | — | 2 | — | — | 1 | — | — | 0.5 | 1 |
| Propylene Glycol | — | — | 2 | — | — | 1 | — | 0.5 | 1 |
| Potassium Chloride | — | — | — | 0.6 | — | — | 0.3 | — | — |
| Trometamol | 1.5 | 1.5 | 1.5 | 1.5 | 1.5 | 1.5 | 1.5 | 1.5 | 1.5 |
| Hydrochloric Acid | q.s. | q.s. | q.s. | q.s. | q.s. | q.s. | q.s. | q.s. | q.s. |
| Citric Acid Hydrate | 0.1 | — | — | — | — | 0.1 | — | — | — |
| Sodium Acetate Hydrate | — | 0.1 | — | — | — | 0.1 | — | — | — |
| Sodium Edetate | — | — | — | 0.1 | — | — | 0.1 | — | — |
| Benzalkonium Chloride | 0.001 | 0.005 | — | 0.001 | 0.005 | 0.01 | 0.001 | 0.005 | — |
| Benzethonium Chloride | — | — | — | — | — | — | — | — | 0.01 |
| Methyl Parahydroxybenzoate | — | — | 0.01 | — | — | — | 0.01 | — | — |
| Propyl Parahydroxybenzoate | — | — | 0.01 | — | — | — | 0.01 | — | — |
| Chlorobutanol | — | — | — | 0.2 | — | — | — | 0.2 | — |
| Polysorbate 80 | 0.3 | — | 0.3 | 0.3 | 0.3 | — | — | 0.3 | 0.3 |
| Polyoxyethylene Castor Oil 60 | — | 0.3 | — | 0.3 | — | 0.3 | — | 0.3 | 0.3 |
| Polyethylene Glycol Monostearate | — | — | 1.5 | 1.5 | — | — | 1.5 | — | 1.5 |
| Purified Water | Total Amount 100 mL | Total Amount 100 mL | Total Amount 100 mL | Total Amount 100 mL | Total Amount 100 mL | Total Amount 100 mL | Total Amount 100 mL | Total Amount 100 mL | Total Amount 100 mL |
| pH | 5 | 5 | 6 | 6 | 6.5 | 6.5 | 4.5 | 4.5 | 4 |

Production Examples 28 to 54

Aqueous compositions of Production Examples 28 to 54 can be produced in accordance with a conventional method as in Production Examples 1 to 27, except that instead of ripasudil monohydrochloride dihydrate, an equal amount of 4-bromo-5-{[(2S)-2-methyl-1,4-diazepan-1-yl]sulfonyl}isoquinoline is used.

INDUSTRIAL APPLICABILITY

In accordance with the present invention, aqueous compositions having excellent preservation stability can be provided, which can be advantageously used in the pharmaceutical industry, for example.

The invention claimed is:

1. An aqueous composition comprising:
   (i) a compound represented by Formula (1):

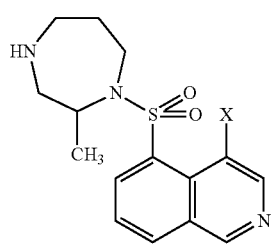

(1)

wherein X represents a halogen atom,
or a salt thereof, or a solvate of the compound or the salt thereof, and
(ii) brimonidine or a salt thereof.

2. The aqueous composition according to claim 1, wherein the compound represented by Formula (1) is ripasudil.

3. The aqueous composition according to claim 1, wherein the compound represented by Formula (1) or a salt thereof or a solvate of the compound or the salt thereof is ripasudil hydrochloride.

4. The aqueous composition according to claim 1, wherein the brimonidine or a salt thereof is brimonidine tartrate.

5. The aqueous composition according to claim 1, which is an ophthalmic agent.

6. The aqueous composition according to claim 1, which is an eye drop.

7. The aqueous composition according to claim 1, which is suitable for preventing and/or treating ocular hypertension and/or glaucoma.

8. A method of treating ocular hypertension, comprising administering the aqueous composition of claim 1 to a subject in need thereof.

9. A method of treating glaucoma, comprising administering the aqueous composition of claim 1 to a subject in need thereof.

* * * * *